United States Patent
Takada et al.

(10) Patent No.: US 8,785,689 B2
(45) Date of Patent: *Jul. 22, 2014

(54) METHOD FOR PURIFYING DIFLUOROACETIC ACID CHLORIDE

(75) Inventors: Naoto Takada, Iruma-gun (JP); Masamune Okamoto, Fujimino (JP); Hideaki Imura, Iruma-gun (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/000,754

(22) PCT Filed: Mar. 28, 2012

(86) PCT No.: PCT/JP2012/058083
§ 371 (c)(1),
(2), (4) Date: Aug. 21, 2013

(87) PCT Pub. No.: WO2012/133501
PCT Pub. Date: Oct. 4, 2012

(65) Prior Publication Data
US 2014/0031588 A1    Jan. 30, 2014

(30) Foreign Application Priority Data

Mar. 28, 2011    (JP) .................... 2011-070387

(51) Int. Cl.
*C07C 51/58*    (2006.01)
*C07C 53/38*    (2006.01)
*C07C 51/64*    (2006.01)
*C07C 53/48*    (2006.01)

(52) U.S. Cl.
CPC ............... *C07C 51/64* (2013.01); *C07C 51/58* (2013.01); *C07C 53/48* (2013.01)
USPC ............................................ 562/861; 562/849

(58) Field of Classification Search
None
See application file for complete search history.

(56) References Cited

U.S. PATENT DOCUMENTS 5,905,169 A    5/1999    Jacobson

FOREIGN PATENT DOCUMENTS

| EP | 0 293 747 A2 | 12/1988 |
| JP | 8-53388 A | 2/1996 |
| JP | 8-92162 A | 4/1996 |
| WO | WO 2011/122341 A1 | 10/2011 |

OTHER PUBLICATIONS

Database Caplus Chemical Abstracts Service, Columbus, Ohio, US; Database Accession No. 152:290546.*
International Search Report dated May 1, 2012 with English translation (four (4) pages).
Japanese-language Written Opinion (PCT/ISA/237) dated May 1, 2012 (five (5) pages).

* cited by examiner

*Primary Examiner* — Karl J Puttlitz
(74) *Attorney, Agent, or Firm* — Crowell & Moring LLP

(57) ABSTRACT

A method for purifying difluoroacetic acid chloride, including the step of bringing a difluoroacetic acid chloride composition that contains at least difluoroacetic acid fluoride into contact with calcium chloride at a temperature enabling reaction thereof thereby converting difluoroacetic acid fluoride into difluoroacetic acid chloride.

10 Claims, No Drawings

METHOD FOR PURIFYING DIFLUOROACETIC ACID CHLORIDE

TECHNICAL FIELD

The present invention relates to a method for purifying difluoroacetic acid chloride useful as an intermediate for pharmaceuticals and agrochemicals and an reagent.

BACKGROUND OF THE INVENTION

As a method for producing difluoroacetic acid chloride, there have been known: (1) a method of chlorinating difluoroacetic acid with a chlorinating agent such as phosphorous pentachloride and the like; (2) a method for oxidizing 1,1-difluoro-2,2-dichloroethane (R-132a) with oxygen under temperatures and pressures (Patent Publication 1); and (3) a method for causing oxidation by irradiating a mixture of 1,1-difluoro-2,2-dichloroethane(R-132a), O2 and Cl2 with a high-pressure mercury lamp (Patent Publication 2).

Additionally, it has been known that difluoroacetic acid fluoride is obtained by subjecting 1-alkoxy-1,1,2,2-tetrafluoroethane to thermal decomposition in the presence of a metal oxide catalyst (Patent Publication 3).

Furthermore, in Patent Publication 4, there is disclosed that benzofluoride having a fluorine-containing substituent is fluorinated with calcium chloride thereby being converted into a corresponding benzochloride.

REFERENCES ABOUT PRIOR ART

Patent Publication

Patent Publication 1: U.S. Pat. No. 5,905,169
Patent Publication 2: Japanese Patent Application Publication No. 8-53388
Patent Publication 3: Japanese Patent Application Publication No. 8-92162
Patent Publication 4: European Patent No. 293747

SUMMARY OF THE INVENTION

Problems to be Solved by the Invention

At the time of producing difluoroacetic acid chloride by oxidizing 1,1-difluoro-2,2-dichloroethane according to the method as discussed in Patent Publication 1 or 2 or the like, by-products such as difluoroacetic acid fluoride and difluoroacetic acid are often formed. Moreover, in a case of converting difluoroacetic acid fluoride into difluoroacetic acid chloride by a halogen-exchange reaction, a small amount of difluoroacetic acid fluoride sometimes remains unreacted. In addition, there are some cases where difluoroacetic acid chloride is decomposed during storage to generate hydrogen fluoride and difluoroacetic acid fluoride is formed by this action.

In view of the above, an object of the present invention is to provide a method for making a difluoroacetic acid chloride composition product that contains difluoroacetic acid fluoride (in the present specification, referred to as "crude difluoroacetic acid chloride" or "crude DFAC") into a highly pure difluoroacetic acid chloride by a simple device.

Means for Solving the Problems

The present inventors studied a method for removing difluoroacetic acid fluoride that accompanies difluoroacetic acid chloride in order to solve the above problems. As a result, it was found that difluoroacetic acid chloride that does not substantially contain difluoroacetic acid fluoride can easily be obtained by bringing crude difluoroacetic acid chloride into contact with a heated anhydrous calcium chloride, with which the present invention had reached completion.

The present invention is as follows.

[Invention 1]

A method for purifying difluoroacetic acid chloride, including the step of
bringing a difluoroacetic acid chloride composition that contains at least difluoroacetic acid fluoride into contact with calcium chloride at a temperature enabling reaction thereof thereby converting difluoroacetic acid fluoride into difluoroacetic acid chloride.

[Invention 2]

A method for purifying difluoroacetic acid chloride, as discussed in Invention 1, wherein the contact includes the step of causing the difluoroacetic acid chloride composition to flow through calcium chloride at a temperature enabling reaction thereof.

Effects of the Invention

In the purification method of the present invention, difluoroacetic acid fluoride contained in a difluoroacetic acid chloride composition is converted into pure difluoroacetic acid chloride, and fluorine atoms that have undergone exchange are fixed in the form of calcium fluoride. Therefore, a highly pure product is obtained without further purification after a treatment conducted according to this method, and the product may be sent into an arbitrary subsequent reaction step.

MODE(S) FOR CARRYING OUT THE INVENTION

The present invention is a method for purifying difluoroacetic acid chloride, including a chlorination step where a difluoroacetic acid chloride composition that contains at least difluoroacetic acid fluoride is brought into contact with calcium chloride at a temperature enabling reaction thereof.

Crude difluoroacetic acid chloride produced or formed by any method is acceptable. It may be exemplified by difluoroacetic acid chloride obtained by oxidizing 1,1-difluoro-2,2-dichloroethane with oxygen, a mixture into which difluoroacetic acid fluoride is mixed (Patent Publications 1 and 2) and the like.

In the purification method of the present invention, crude difluoroacetic acid chloride is purified in such a manner as to bring it into contact with calcium chloride at a temperature enabling reaction thereof to convert difluoroacetic acid fluoride into difluoroacetic acid chloride.

The reaction relating to the purification method of the present invention is represented by the following equation.

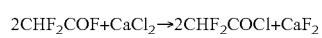

$$2CHF_2COF + CaCl_2 \rightarrow 2CHF_2COCl + CaF_2$$

As shown in the above equation, difluoroacetic acid fluoride is converted into pure difluoroacetic acid chloride and therefore a further purification operation is not necessary, while fluorine atoms removed by halogen-exchange are fixed in the form of calcium fluoride so that waste treatment and the like can easily be carried out.

The content of difluoroacetic acid fluoride contained in crude difluoroacetic acid chloride is not limited. From a practical standpoint, it is preferably less than 50 mass %, more preferably less than 20 mass %, much more preferably less than 10 mass % of the crude difluoroacetic acid chloride.

Additionally, it is further preferable that the content of difluoroacetic acid fluoride is previously adjusted to be less than 1 mass %.

Calcium chloride ($CaCl_2$) used in the purification method of the present invention is preferably anhydride. In particular, calcium chloride products for general purpose use, which are not required to be high in purity and commercially available as a reagent, a raw material for chemicals and a drying agent, may be used. In the case of using calcium chloride having crystalline water, it is preferable that a pretreatment is conducted, where the crystalline water is removed in advance at 300° C. or more under the flow of nitrogen and the like. The form may freely be selected, but the powder form is preferable when the reaction system is a fluidized bed type or batch type, while the granular form is preferable when calcium chloride is used under a flow system. Though the grain size is not particularly limited and depends on the shape of the reactor or on the tube diameter in particular, it is preferable to use granular calcium chloride consisting chiefly of grains having a size of around 1-20 mm at the maximum because it is easy to handle.

The reaction system may freely be selected and therefore it may be either the liquid phase or the gas phase, but the reaction is preferably conducted in the gas phase. Though it is also possible to adopt a batch type or a flow type, the flow type system is preferable in view of operational convenience. A reaction in the liquid phase is conducted at low temperatures and high pressures in order to liquefy difluoroacetic acid fluoride, which is economically disadvantageous. Moreover, in the case of forming the liquid phase by using a solvent, it is necessary to remove the solvent after treatment. Therefore, the method of the present invention is preferably performed in the gas phase continuous style.

In the flow system, the method of the present invention serves as a method for flowing crude difluoroacetic acid chloride that contains difluoroacetic acid fluoride through granular calcium chloride at a temperature sufficient for difluoroacetic acid fluoride to convert into difluoroacetic acid chloride, i.e., a temperature enabling the reaction, in which difluoroacetic acid fluoride is converted into difluoroacetic acid chloride quantitatively. By the way, this reaction is a gas-solid reaction where a solid usually contributes to the reaction only at its surface and therefore its inner portion does not contribute to the reaction in most cases; however, granular calcium chloride used in the present reaction can contribute to the reaction substantially at all of the portion including the inner portion of a grain of calcium chloride, and can maintain its original shape without causing a remarkable powdering.

The reaction temperature depends on treatment conditions including the retention time and the like, and it preferably 50 to 250° C. and more preferably 100 to 200° C. The retention time depends on the reaction temperature and it preferably 1 to 1000 seconds, more preferably 10 to 700 seconds, much more preferably 50 to 500 seconds. A reaction shorter than 1 second may sometimes not terminate and therefore not preferable. A reaction over 1000 seconds may proceed but it does not preferable since the throughput is reduced. Pressure to be applied during the reaction may freely be determined, but an operation conducted substantially at atmospheric pressure without increasing or reducing the pressure is preferable. When a reaction tube is used in the flow system and the content of DFAF is high, a localized heated state (a heat spot) of 10-30° C. occurs in the vicinity of the inlet at the initial stage of the reaction and then the heat spot gradually shifts toward the outlet. With this phenomenon, the consumption of calcium chloride is noticed and the timing of its replacement can be determined thereby. To use an apparatus relatively large within the scope of a person having ordinary skill in the art is preferable because the frequency of the replacement of calcium chloride is reduced. It is preferable that the reaction tube is formed of stainless steel, Monel (registered trademark), Inconel (registered trademark), Hastelloy (registered trademark), fluorocarbon polymers or a material obtained by conducting lining on the above materials. A larger ratio between the tube length and the tube diameter of the reaction tube is to improve the purification efficiency but the increase of the ratio accelerates pressure drop, so that the ratio is preferably 5 to 200.

In the reaction, it is also possible to contain argon, nitrogen, hydrogen and the like as a carrier gas. The thus obtained difluoroacetic acid chloride can be provided directly as a product without a further purification, or alternatively, can be used as a reagent for various reactions without a further purification.

Calcium fluoride that the reaction forms as a by-product may be used as a material for producing an optical crystal or hydrogen fluoride.

EXAMPLES

Hereinafter, the present invention will be explained with reference to examples; however, the present invention is not limited to these examples. Analysis of organic substances was performed by gas chromatography (Flame Ionization Detector) and the composition was expressed in terms of area % (hereinafter indicated by "%").

Example 1

A reaction tube formed of stainless steel and having an inner diameter of 37 mm and a length of 1000 mm was charged with 150 g of anhydrous calcium chloride available from JUNSEI CHEMICAL CO., LTD. (grain size: about 2.5-3.5 mm) and heated by a tape heater to 200° C. under the flow of nitrogen. After the temperature was stabilized at 200° C., crude difluoroacetic acid chloride (DFAC, 95.0% purity) containing 4.8% of difluoroacetic acid fluoride (DFAF) was started to flow at a rate of 0.2 g/min, and simultaneously the supply of nitrogen was suspended. Organic substances (98 g) recovered after the flow of 100 g of the crude difluoroacetic acid chloride at a dry ice trap connected to the outlet of the reaction tube was subjected to analysis by gas chromatography. As a result, the purity of DFAC was 99.9% and a trace amount (lower than 0.001%) of DFAF was confirmed.

Example 2

(Preparation of DFAC)

A 1000 cc autoclave formed of stainless steel and equipped with a stirrer was charged with lithium chloride (LiCl, 168.7 g, 4.0 mol) and then the inner section was decompressed. After cooling the autoclave in an acetone-dry ice bath until the internal temperature reached −40° C., DFAF (300 g, 3.06 mol) containing a small amount of monofluoromethane was introduced thereinto with pressure while stirring. Thereafter, the bath was removed and the autoclave was stirred for 1 hour at room temperature (about 25° C.), followed by taking 1 hour to increase the temperature to 70° C. by a band heater and then letting the autoclave stand for 4 hours. Pressure applied at this time was 0.56 MPaG (gage pressure). After the reaction had terminated, the content was recovered and subjected to flash distillation. As a result of conducting analysis by gas chromatography, the content was found to be DFAC ($CHF_2COCl$) of 98.64% purity (recovery rate: 96%). It was confirmed that impurities consisted chiefly of 0.36% of $CH_3F$ derived from impurities contained in the starting material DFAF; 0.15% of unreacted DFAF; and 0.33% of difluoroacetic acid ($CHF_2COOH$).

(Purification)

By using the thus obtained crude DFAC, the same experiment as in

Example 1 was repeated. More specifically, Organic substances (103 g) recovered after the flow of 100 g of the crude DFAC at a dry ice trap connected to the outlet of the reaction tube was subjected to analysis by gas chromatography. As a result, the purity of DFAC was 99.9% and a trace amount (lower than 0.001%) of DFAF was confirmed.

Industrial Applicability

The present invention is useful as a method for purifying difluoroacetic acid chloride useful as an reagent for introducing a difluoromethyl group.

The invention claimed is:

1. A method for purifying difluoroacetic acid chloride, comprising the step of:
    bringing a difluoroacetic acid chloride composition that contains at least difluoroacetic acid fluoride into contact with calcium chloride at a temperature enabling reaction thereof thereby converting difluoroacetic acid fluoride into difluoroacetic acid chloride.

2. A method for purifying difluoroacetic acid chloride, as claimed in claim 1, wherein the contact comprises the step of causing the difluoroacetic acid chloride composition to flow through calcium chloride at a temperature enabling reaction thereof.

3. A method for purifying difluoroacetic acid chloride, as claimed in claim 1, wherein the reaction temperature is 50 to 250° C.

4. A method for purifying difluoroacetic acid chloride, as claimed in claim 1, wherein the retention time is 1 to 1000 seconds.

5. A method for purifying difluoroacetic acid chloride, as claimed in claim 1, wherein the reaction is conducted in a liquid phase.

6. A method for purifying difluoroacetic acid chloride, comprising the step of:
    reacting difluoroacetic acid fluoride with lithium chloride thereby producing a difluoroacetic acid chloride composition that contains at least difluoroacetic acid fluoride; and
    bringing the difluoroacetic acid chloride composition into contact with calcium chloride at a temperature enabling reaction thereof thereby converting difluoroacetic acid fluoride into difluoroacetic acid chloride.

7. A method for purifying difluoroacetic acid chloride, as claimed in claim 6, wherein the contact comprises the step of causing the difluoroacetic acid chloride composition to flow through calcium chloride at a temperature enabling reaction thereof.

8. A method for purifying difluoroacetic acid chloride, as claimed in claim 6, wherein the reaction temperature is 50 to 250° C.

9. A method for purifying difluoroacetic acid chloride, as claimed in claim 6, wherein the retention time is 1 to 1000 seconds.

10. A method for purifying difluoroacetic acid chloride, as claimed in claim 6, wherein the reaction is conducted in a liquid phase.

* * * * *